(12) United States Patent
Konkle et al.

(10) Patent No.: US 8,975,868 B2
(45) Date of Patent: Mar. 10, 2015

(54) CHARGING STATION FOR PORTABLE X-RAY DETECTORS

(75) Inventors: Nicholas Ryan Konkle, Waukesha, WI (US); Habib Vafi, Brookfield, WI (US)

(73) Assignee: General Electric Company, Schenectady, NY (US)

(*) Notice: Subject to any disclaimer, the term of this patent is extended or adjusted under 35 U.S.C. 154(b) by 561 days.

(21) Appl. No.: 13/308,354

(22) Filed: Nov. 30, 2011

(65) Prior Publication Data

US 2013/0134930 A1 May 30, 2013

(51) Int. Cl.
*H01M 10/46* (2006.01)

(52) U.S. Cl.
USPC .......................................... 320/115

(58) Field of Classification Search
CPC ....... H02J 7/0045; H02J 7/0042; H02J 7/025; H02J 7/0016; H02J 7/0021
USPC ......... 320/107, 108, 110, 114, 115, 116, 132; 378/101, 189, 204, 205
See application file for complete search history.

(56) References Cited

U.S. PATENT DOCUMENTS

| 7,785,005 | B2 | 8/2010 | Bettouyashiki et al. | |
| 7,884,573 | B1* | 2/2011 | Larsen | 320/110 |
| 2010/0141206 | A1* | 6/2010 | Agassi et al. | 320/109 |

* cited by examiner

*Primary Examiner* — Edward Tso
(74) *Attorney, Agent, or Firm* — Fletcher Yoder, P.C.

(57) ABSTRACT

A charging station for a portable X-ray detector is described. In one embodiment, the charging station includes one or more biasing members that act to guide and align a portable detector when inserted into the charging station. In certain embodiments, a physical, pin-type connector for connecting to an inserted portable detector is present, while in other embodiments no pin-type connector is present.

14 Claims, 4 Drawing Sheets

CHARGING STATION FOR PORTABLE X-RAY DETECTORS

BACKGROUND

A number of non-invasive imaging approaches are known and are presently in use. One such type of system is based upon the detection of X-rays that have passed through a volume of interest. The X-rays traverse the volume, and whatever materials occupy the volume, and impact a film or a digital detector. In medical diagnostic contexts, for example, such systems may be used to visualize internal tissues and diagnose patient ailments. In other contexts, parts, baggage, parcels, and other materials may be imaged to assess their contents or for other purposes, such as for quality review in a manufacturing context.

Increasingly, such X-ray systems use digital circuitry, such as solid-state detectors, for detecting the X-rays. Such solid-state detectors may generate electrical signals indicative of the incident X-rays on the detector, which in turn are indicative of the attenuation or scatter of X-rays along different ray paths through the imaged volume. The generated signals may in turn be processed to reconstruct images of the subject of interest within the volume, including internal features of an object or patient within the imaged volume.

Such solid-state or digital detectors may be portable and may be used in place of film-based detection systems as a means of upgrading an existing system. In addition, in newer systems, a variety of portable detectors may be provided and used interchangeably with different systems, such that no one detector is fixed to or dedicated for use with a particular imaging system. In such arrangements, a portable detector may need to be stored or otherwise physically accounted for when not in use.

BRIEF DESCRIPTION

In accordance with one embodiment, a charging station is provided. The charging station is configured to charge portable radiation detectors and comprises one or more detector slots. Each detector slot is capable of holding different sizes of portable radiation detectors. Each detector slot comprises a housing connector configured to connect to a complementary connector of a portable radiation detector when the portable radiation detector is inserted into the respective detector slot. Each detector slot also comprises one or more biasing members disposed within each detector slot. The one or more biasing members are configured to bias the portable radiation detector, when the portable radiation detector is inserted into the respective detector slot, such that the housing connector and the complementary connector are aligned.

In a further embodiment, a charging station is provided. The charging station is configured to charge portable radiation detectors and comprises one or more detector slots. Each detector slot is capable of holding different sizes of portable radiation detectors. Each detector slot comprises a non-pin interaction region configured to transfer power to a portable radiation detector via electromagnetic or field effects when the non-pin interaction region is proximate to a complementary region of the portable radiation detector.

In an additional embodiment, a monitor for use with a charging station is provided. The monitor comprises a screen configured to display information about one or more portable radiation detectors associated with the charging station.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

As discussed herein, portable digital X-ray detectors may be used with, and exchanged between, various radiological imaging systems, including legacy systems originally intended for use with film cassettes. Such a portable detector, unlike a film-based detector cassette, typically operates on battery or other power and may be charged periodically to be ready for use. In addition, because a portable detector is not attached or affixed to a particular system, storage may be provided for such portable detector, as discussed herein, so the location of a portable detector is known and it may be retrieved for use when needed. With this in mind a charging station or storage hub is discussed herein for use with portable X-ray detectors.

With the foregoing in mind, one or more specific embodiments of a suitable charging station and/or storage bin will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosed subject matter, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
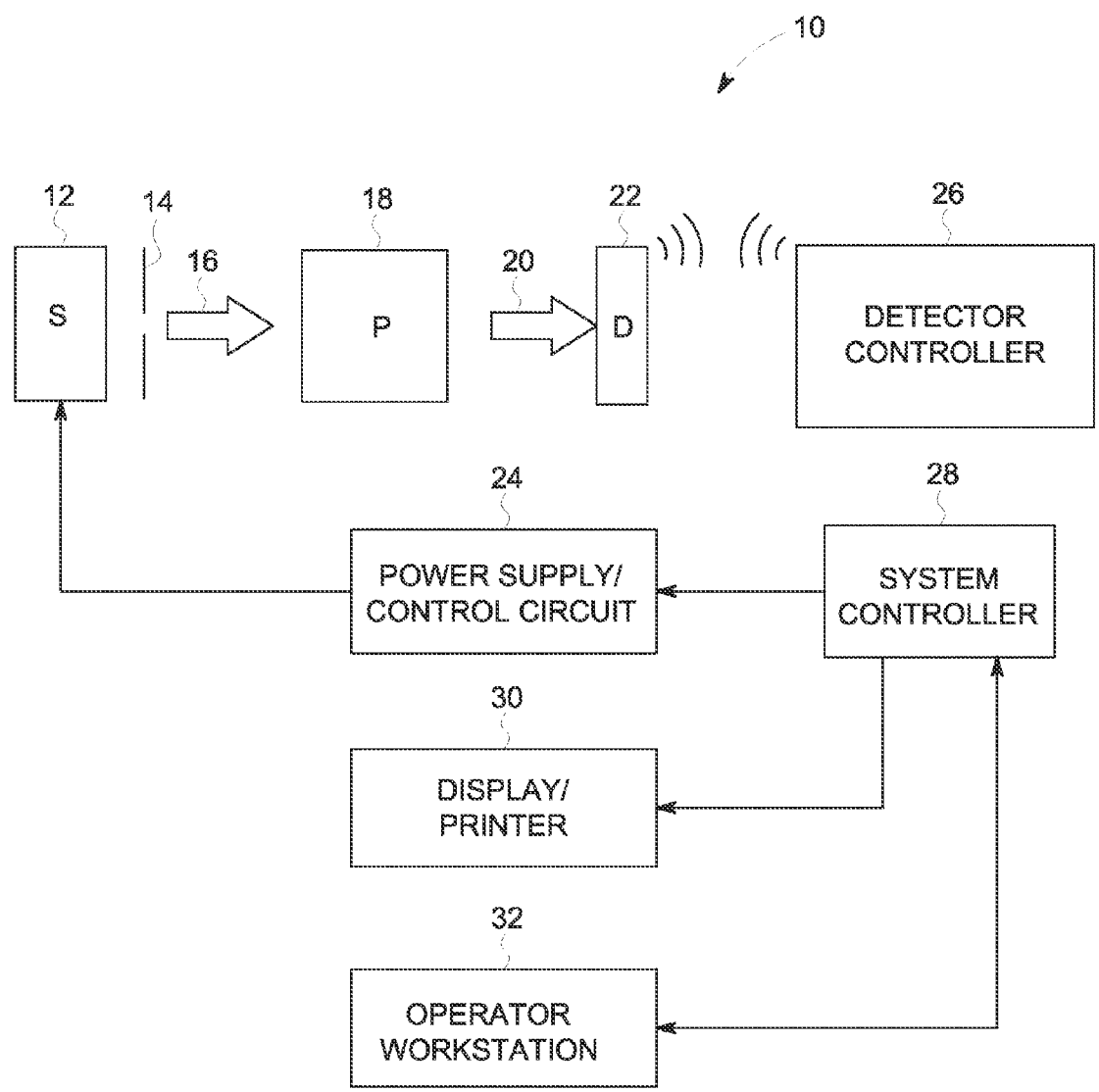
FIG. 1 is a diagrammatical overview of a digital X-ray imaging system in accordance with one or more embodiments of the present disclosure.

With the foregoing comments in mind and turning to FIG. 1, this figure illustrates diagrammatically an example of an imaging system 10 for acquiring and processing image data using a portable detector as discussed herein. In the illustrated embodiment, the imaging system 10 is an X-ray system designed both to acquire original image data and to process the image data for display. In the embodiment illustrated in FIG. 1, imaging system 10 includes a source of X-ray radiation 12 positioned adjacent to a collimator 14 that shapes and/or limits a stream of radiation 16 that passes into a region in which an object or subject, such as a patient 18, is positioned. A portion of the radiation 20 passes through or around the subject and impacts a portable digital X-ray detector, represented generally at reference numeral 22. The portable detector 22 may convert the X-ray photons incident on its surface to lower energy photons, and subsequently to electric signals, which are acquired and processed to reconstruct an image of the features within the subject.

In one example of an imaging system 10, the radiation source 12 is controlled by a power supply/control circuit 24 which supplies both power and control signals for examination sequences. Moreover, the portable detector 22 is communicatively coupled to a detector controller 26 which commands acquisition of the signals generated in the portable detector 22. In the depicted example, the portable detector 22 communicates wirelessly with the detector controller 26 via a suitable wireless communication standard. In other embodiments, the portable detector 22 can communicate with the detector controller 26 over a wire or cable.

In one embodiment, the detector controller 26 may be a handheld device or controller that allows a user to control operation of the portable detector 22, such as to place the detector 22 in a receptive state where incident radiation on the detector 22 may be measured or in a standby or idle state when an image operation is not currently being performed or is not imminent. In such implementations, the detector controller 26 may be controlled by a user, without further communication with the other components of the imaging system 10. In other embodiments, the detector controller 26 may communicate with a system controller 28, discussed below, to coordinate operation and readout of the portable detector 22 with the operation of the other components of the system 10, such as source 12.

The power supply/control circuit 24 is responsive to signals from a system controller 28. In some implementations, the detector controller 26 may also be responsive to signals from the system controller 28. In general, the system controller 28 commands operation of the imaging system 10 to execute examination protocols and, in some instances, to process acquired image data. For example, in some embodiments the system controller 28 may include signal processing circuitry, typically based upon a programmed general purpose or application-specific digital computer; and associated manufactures, such as optical memory devices, magnetic memory devices, or solid-state memory devices, for storing programs and routines executed by a processor of the computer to carry out various functionalities, as well as for storing configuration parameters and image data; interface protocols; and so forth. In one embodiment, a general or special purpose computer system may be provided with hardware, circuitry, firmware, and/or software for performing the functions attributed to one or more of the power supply/control circuit 24, the detector controller 26, and/or the system controller 28 as discussed herein.

In the embodiment illustrated in FIG. 1, the system controller 28 is linked to at least one output device, such as a display or printer as indicated at reference numeral 30. The output device may include standard or special purpose computer monitors and associated processing circuitry. One or more operator workstations 32 may be included in or otherwise linked to the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
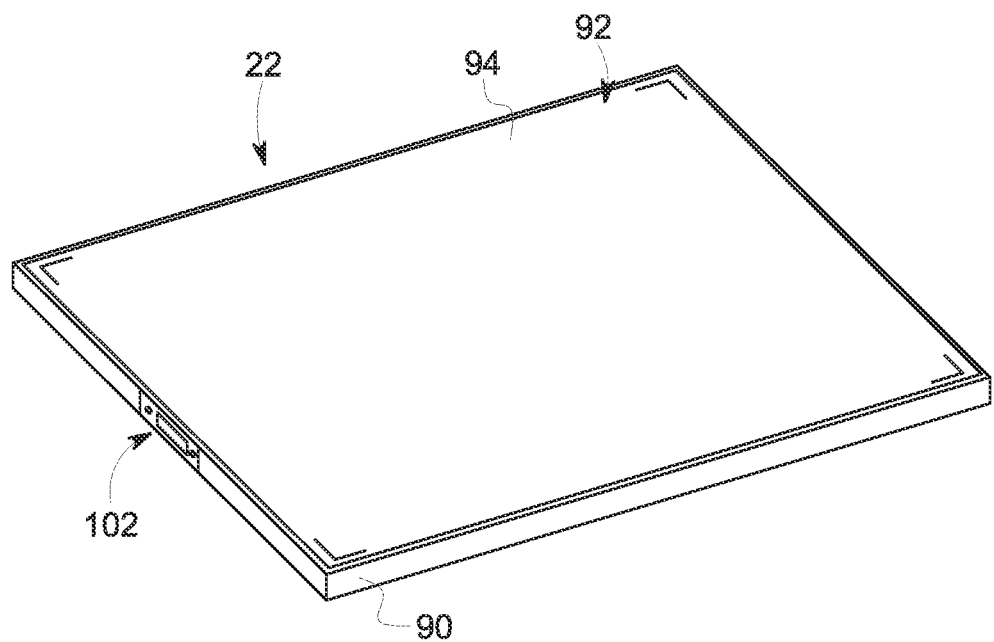
FIG. 2 is a perspective view of a portable digital detector, in accordance with aspects of the present disclosure.

With the foregoing discussion of imaging systems in mind, it should be appreciated that such systems may be used in conjunction with a portable detector 22, as discussed herein. An example of one embodiment of a portable detector 22 is generally illustrated in FIG. 2. In the illustrated embodiment, the portable detector 22 may include a housing 90 that encloses various components of the detector 22. In certain embodiments, the housing 90 includes a window 92 that exposes a surface of the solid-state detector array 94 on which radiation is directed during use. As discussed above, when in use, the detector array 94 may be configured to receive electromagnetic radiation, such as from the radiation source 12, and to convert the radiation into electrical signals that may be interpreted by the imaging system 10 to output an image of an object or patient 18.

In one embodiment, operating power may be provided to the portable detector 22 via a removable or non-removable battery or by a cable (e.g., a tether). Further, in one embodiment, the portable detector 22 may communicate with one or more other components of the imaging system 10, such as the detector controller 26, via a wireless transceiver disposed within the body of the portable detector 22.

The portable detector 22 may also include a docking connector 102. In one embodiment, the docking connector 102 may be positioned on the portable detector 22 so as to engage a complementary structure in a charging or storage station, as discussed herein. In this manner, the docking connector 102 may be used to provide power to the detector 22 and to allow data communication (such as gigabit Ethernet communication) between the detector 22 and other components of an imaging system.

To the extent that portable detectors 22 may be employed that are not affixed or assigned to a particular X-ray imaging system 10 and/or which are used in place of film-based cassettes, the portable detectors 22 may be stored or charged separately from the imaging systems 10 with which the detectors 22 are used. With this in mind, a storage and/or charging station may be provided where various portable detectors 22 are stored when not in use. For example, a portable detector 22 may be stored in a charging station 120 or receptacle specifically configured to receive the portable detector 22. One example of such a station 120 is depicted in FIG. 3, which depicts a perspective view of a charging station 120 configured to hold, charge, and monitor portable detectors 22 placed therein.

Figure 3:
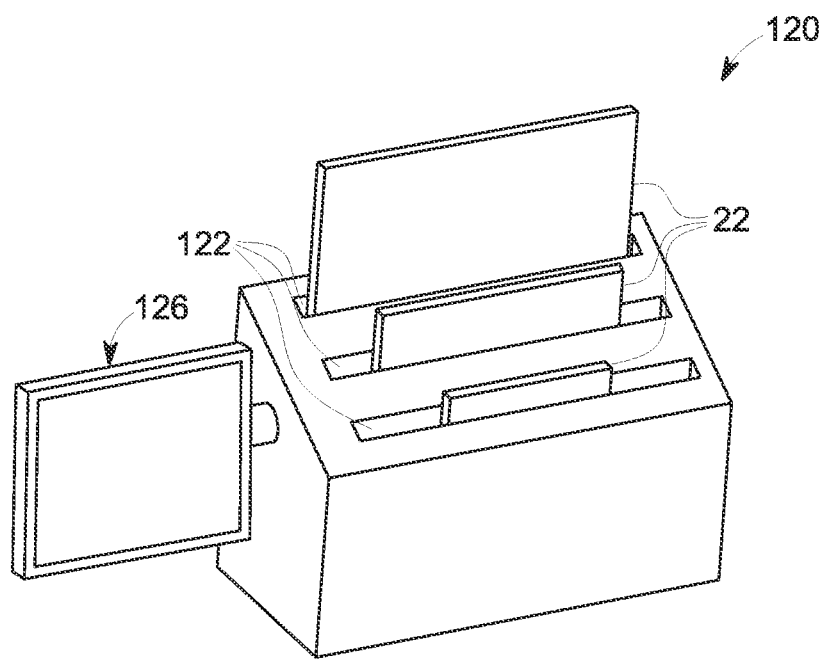
FIG. 3 depicts one embodiment of a charging station, in accordance with aspects of the present disclosure.

As illustrated in FIG. 3, the station 120 may include one or more detector slots 122 configured to receive portable detectors 22. In certain embodiments, the detector slots 122 may be sized so that differently sized portable detectors 22 can be accommodated within a slot 122. For example, portable detectors 22 used as replacements for film detector cassettes may be sized in accordance with the various standards for such cassettes. In such an embodiment, a detector slot 122 may be sized to accept portable detectors 22 of different sizes.

In the depicted embodiment, the charging station 120 also includes a monitor 126 that may be used to display information about the charging station 120 and/or about one or more portable detectors 22 associated with the station 120. In certain embodiments, the monitor 126 may be non-removably attached to the charging station 120. However, in other embodiments, the monitor 126 may be a removable structure, such as a tablet computer or other standalone computing device that includes a screen and which may provide input capabilities (such as a touchscreen or button inputs). In embodiments where the monitor 126 is detachable, the monitor 126 may provide monitoring or other information about one or more portable detectors 22 even when not attached to the charging station 120, e.g., when remote from the station 120, such as via wireless network, radiofrequency (RF), Bluetooth, or other suitable communications standards.

Figure 4:
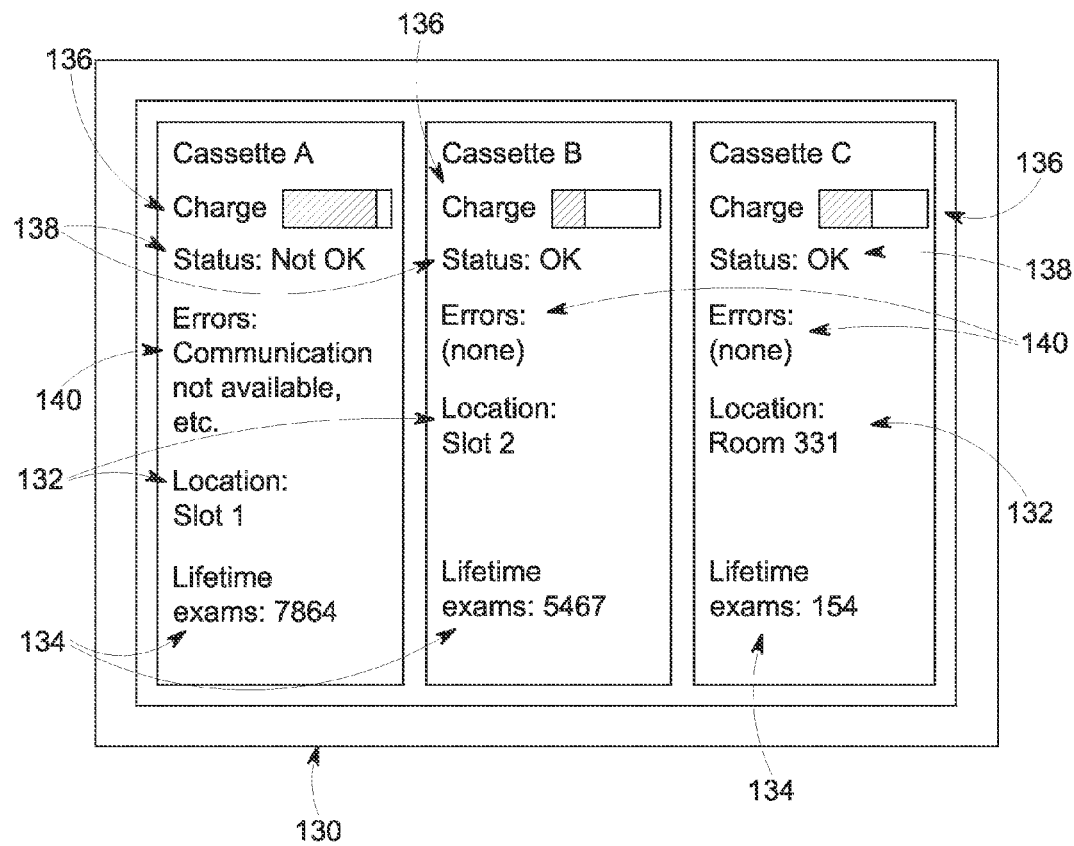
FIG. 4 depicts an example of a screen shot of a monitor associated with the charging station of FIG. 3.

By way of example, and turning to FIG. 4, a sample screen for display on a monitor 126 is provided. In this example, the monitor 126 displays information about different portable detectors associated with the charging station, including current location 132, usage history 134, charge status 136, detector status 138, and current error codes 140. As will be appreciated, other information may also be provided by the monitor 126, such as the length of time a portable detector 22 has been removed from a charge station 120, the name or identifying code of the personnel who removed (i.e., checked out) a portable detector 22, and so forth.

In certain embodiments, the detectors slots 122 may include one or more features to help align different sized portable detectors 22 inserted into a slot 122, such as to align a connector 102 on such portable detectors 22 with a housing connector 150 disposed within a detector slot 122. The housing connector 150 may be configured to provide power to the portable detector 22 (such as to charge the portable detector 22) and/or may be configured to make a data connection with the portable detector 22 (such as to read out data stored on the portable detector 22 or to access logs or status information of the portable detector 22).

Figures 5, 6:
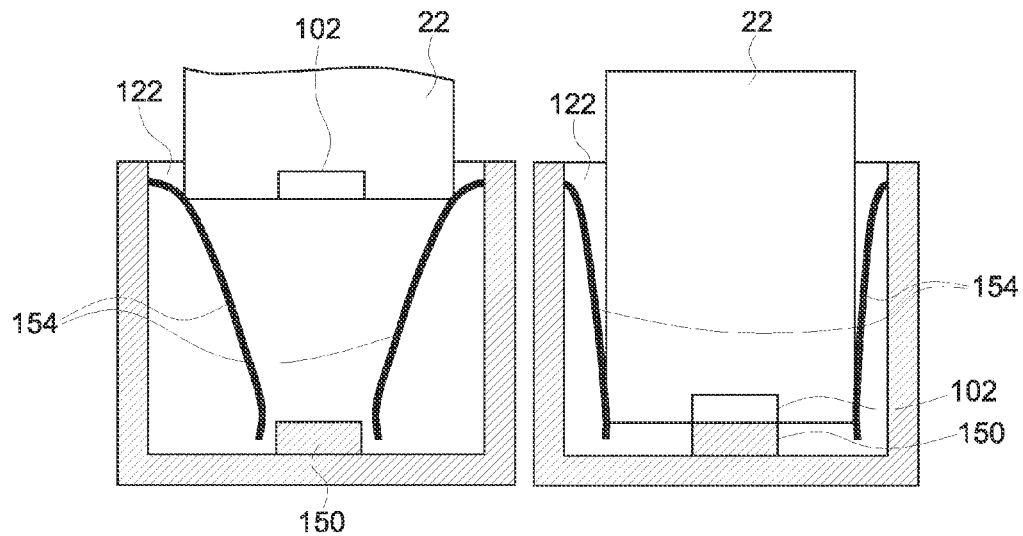
FIG. 5 depicts a cut-away view of a portable detector of a first size being inserted into a detector slot of a charging station in accordance with one embodiment.
FIG. 6 depicts a cut-away view of the portable detector of the first size when inserted into the detector slot of the charging station of FIG. 3.

For example, turning to FIGS. 5 and 6, a portable detector 22 of a first size may be inserted into a detector slot 120 having spring guides 154 (such as guides composed of spring steel) or other biasing members (such as stiff, spring-loaded guides) that act to position the portable detector 22 so that the connector 102 of the portable detector 22 properly mates with the housing connector 150 within the detector slot 122. That is the spring guides 154 or other biasing members may provide a guiding force that acts to position the portable detector within the slot 122 as the portable detector 22 is placed within the slot 122.

Figures 7, 8:
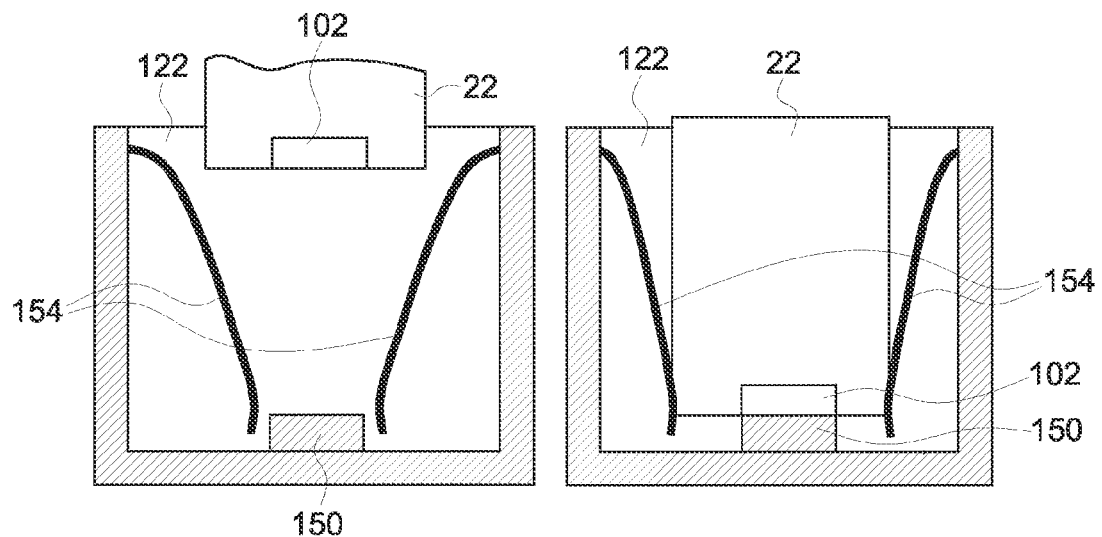
FIG. 7 depicts a cut-away view of a portable detector of a second size being inserted into a detector slot of a charging station in accordance with one embodiment.
FIG. 8 depicts a cut-away view of the portable detector of the second size when inserted into the detector slot of the charging station of FIG. 7.

Turning to FIGS. 7 and 8, the spring guides 154 or other biasing members may be positioned or sized so that other sizes of portable detector 22, such as the smaller detector depicted in FIGS. 7 and 8, also contact and are guided by the spring guides 154 or biasing members to be properly positioned within the detector slot 122, such as to make connection with the housing connector 150. For example, in an instance where a smaller portable detector 22 is inserted into the detector slot 122, as depicted, the guides 154 may be deflected less than when a larger detector 22 is inserted, but the guides 154 will still act to guide the portable detector within the slot 122. In this manner, whatever size of portable detector 22 is inserted into the detector slot 122, a connector 102 of the inserted portable detector 22 will be aligned so as to mate with the complementary housing connector 150 within the detector slot 122.

While the preceding examples depict a connector 102 and complementary housing connector 150 that are centered, respectively, on the portable detector 22 and within the detector slot 122, such an arrangement is depicted merely to facilitate explanation. In other embodiments, the housing connector 150 and connector 102 may be offset from a centered position in the slot 122 and/or on the detector 22. In such arrangements, the size, placement, and/or stiffness of the guiding or biasing members 154 may be configured as to properly guide an inserted portable detector so that the connector 102 and housing connector 150 align. Further, in certain embodiments, one or both of the connector 102 or housing connector 150 may be magnetized such that the magnetic attraction associated with one or both of the connector 102 or housing connector 150 further aid in the alignment and connection process.

While the preceding example describe the use of a pin-type connector or other connector employing a physical engagement, in other embodiments no pin-type or metal-to-metal engagement may be employed. For example, turning to FIGS. 9 and 10 in other embodiments, an electromagnetic (EM) coupling and/or use of inductive or magnetic field effects may be utilized for power and/or data transfer by bringing corresponding detector regions 170 and detector slot regions 172 into proximity or contact with one another. Such EM coupling or use of field effects may be used to power or charge the portable detector 22 and/or to achieve data transfer with the portable detector 22, as discussed above.

Figures 9, 10:
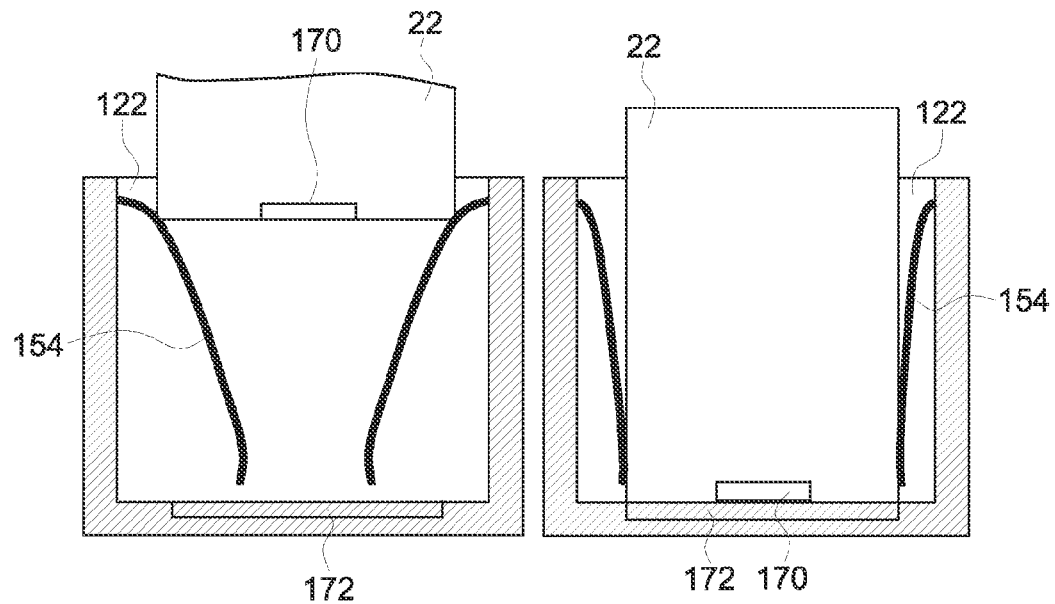
FIG. 9 depicts a cut-away view of a portable detector of a first size being inserted into a detector slot of a charging station having a non-pin connection, in accordance with one embodiment.
FIG. 10 depicts a cut-away view of the portable detector of the first size when inserted into the detector slot of the charging station of FIG. 9.

In certain such embodiments, the detector region 170 and/or the detector slot regions 172 used to achieve the EM coupling or field effects need not be localized, as depicted with respect to the detector slot region 172 in FIGS. 9 and 10. That is, the corresponding detector region 170 may be brought into proximity or contact with the detector slot region 172 anywhere along the length of the detector slot region 172. Therefore, in such embodiments, the guiding or biasing members 154 may be absent if it is otherwise not desired or useful to center or otherwise control the placement of the portable detector 22 within the detector slot 122. Further, in one such embodiment, a sidewall or edge of the detector slot 122 may be magnetized to attract a portable detector 22 placed within the slot 122 and to keep inserted detectors 22 aligned within the respective slots 122.

This written description uses examples to disclose the present subject matter, including the best mode, and also to enable any person skilled in the art to practice the disclosed subject matter, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A charging station configured to charge portable radiation detectors, comprising:
one or more detector slots, each capable of holding different sizes of portable radiation detectors, each detector slot comprising:
a housing connector configured to connect to a complementary connector of a portable radiation detector when the portable radiation detector is inserted into the respective detector slot; and
one or more biasing members disposed within each detector slot, the one or more biasing members configured to contact the portable radiation detector and to bias the portable radiation detector, when the portable radiation detector is inserted into the respective detector slot, such that the housing connector and the complementary connector are aligned.

2. The charging station of claim 1, wherein the housing connector is capable of charging the portable radiation detector, when the portable radiation detector is inserted into the respective detector slot.

3. The charging station of claim 1, wherein the housing connector is capable of transferring data from the portable radiation detector, when the portable radiation detector is inserted into the respective detector slot.

4. The charging station of claim 1, comprising a monitor configured to display information about an associated portable radiation detector.

5. The charging station of claim 4, wherein the monitor comprises a detachable monitor configured to be removed from the charging station.

6. The charging station of claim 1, wherein the one or more biasing members comprise spring guides or spring-loaded guides.

7. The charging station of claim 1, wherein the one or more biasing members center the portable radiation detector, when the portable radiation detector is inserted into the respective detector slot.

8. The charging station of claim 1, wherein the one or more biasing members do not center the portable radiation detector, when the portable radiation detector is inserted into the respective detector slot.

9. A charging station configured to charge portable radiation detectors, comprising:
one or more detector slots, each capable of holding different sizes of portable radiation detectors, each detector slot comprising:
an engagement region configured to transfer power to a portable radiation detector via electromagnetic or field effects when the engagement region is proximate to a complementary region of the portable radiation detector, wherein there is no metal-to-metal engagement between the engagement region and the complementary region.

10. The charging station of claim 9, comprising one or more biasing members disposed within each detector slot, the one or more biasing members configured to bias the portable radiation detector when the portable radiation detector is inserted into the respective detector slot.

11. The charging station of claim 9, comprising one or more magnetic surfaces configured to align the portable radiation detector when the portable radiation detector is inserted into the respective detector slot.

12. The charging station of claim 9, comprising a monitor configured to display information about an associated portable radiation detector.

13. The charging station of claim 12, wherein the monitor comprises a detachable monitor configured to be removed from the charging station.

14. The charging station of claim 9, wherein the non-pin interaction region is longer in a first dimension than the corresponding length of the complementary region of a respective portable radiation detector.

* * * * *